(12) United States Patent
Chandler

(10) Patent No.: US 6,555,390 B2
(45) Date of Patent: *Apr. 29, 2003

(54) CHROMATOGRAPHIC ASSAY OR TEST DEVICE

(76) Inventor: Howard Milne Chandler, 857 Princes Point Rd., Yarmouth, MA (US) 04096

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,051
(22) PCT Filed: Jun. 27, 1997
(86) PCT No.: PCT/AU97/00408
§ 371 (c)(1), (2), (4) Date: May 10, 1999
(87) PCT Pub. No.: WO98/00712
PCT Pub. Date: Jan. 8, 1998

(65) Prior Publication Data
US 2002/0004245 A1 Jan. 10, 2002

(30) Foreign Application Priority Data
Jun. 28, 1996 (AU) ............................................. PO0713

(51) Int. Cl.⁷ ............................................. G01N 33/543
(52) U.S. Cl. ................ 436/518; 436/514; 436/501; 436/524; 436/527; 436/528; 436/530; 436/538; 436/541; 436/807; 436/810; 436/814; 436/823; 436/169; 435/4; 435/7.1; 435/287.1; 435/287.2; 435/287.8; 435/287.7; 435/287.9; 435/803; 435/805; 435/810; 435/970; 422/61; 422/56; 422/58

(58) Field of Search .............................. 422/61, 56, 58; 435/4, 7.1, 287.1, 287.2, 287.7, 287.8, 287.9, 803, 805, 810, 970; 436/501, 518, 524, 527, 528, 530, 538, 541, 807, 810, 814, 823, 169, 514

(56) References Cited

U.S. PATENT DOCUMENTS 4,409,988 A * 10/1983 Greenspan .................. 128/759
5,137,808 A * 8/1992 Ullman et al. ............... 435/7.9
5,169,789 A * 12/1992 Bernstein .................... 436/501

(List continued on next page.)

FOREIGN PATENT DOCUMENTS

EP   A 0269362     6/1988
WO   WO A 92/21977  12/1992

(List continued on next page.)

*Primary Examiner*—Christopher L. Chin
*Assistant Examiner*—Pensee T. Do
(74) *Attorney, Agent, or Firm*—Lahive & Cockfield, LLP

(57) ABSTRACT

A chromatographic assay or test device for detection and/or determination of an analyte in a test sample, comprises a base member, and a chromatographic medium located in or on said base member, the base member being provided with a receptacle to receive an applicator having the sample applied thereto, and the applicator being movable when located in said receptacle between a first position in which the applicator is out of fluid contact with the chromatographic medium, and a second position in which the applicator is in fluid contact with the chromatographic medium so as to apply a sample on the applicator to the chromatographic medium. In an alternative aspect, the test device comprises a base member, and a second member, at least one of the base member and the second member including a chromatographic medium, and the second member being slidably movable with respect to the base member from a first position to a second position.

25 Claims, 10 Drawing Sheets

U.S. PATENT DOCUMENTS

| | | | |
|---|---|---|---|
| 5,200,317 A | * 4/1993 | Georgevich | 435/7.4 |
| 5,415,994 A | 5/1995 | Imrich et al. | |
| 5,416,000 A | * 5/1995 | Allen et al. | 435/7.92 |
| 5,468,648 A | * 11/1995 | Chandler | 436/518 |
| D367,236 S | * 2/1996 | Groothuizen et al. | D10/46 |
| 5,504,013 A | * 4/1996 | Senior | 436/165 |
| 5,607,863 A | * 3/1997 | Chandler | 436/518 |
| 5,611,995 A | * 3/1997 | De Zoeten et al. | 422/58 |
| 5,824,268 A | * 10/1998 | Bernstein et al. | 422/56 |
| 5,869,345 A | * 2/1999 | Chandler | 436/514 |
| 5,877,028 A | * 3/1999 | Chandler et al. | 436/514 |
| 5,882,942 A | * 3/1999 | Kagaya | 436/174 |
| 5,980,828 A | * 11/1999 | McClintock et al. | 422/58 |
| 6,027,943 A | * 2/2000 | Kang et al. | 436/518 |
| 6,184,040 B1 | * 2/2001 | Polizzotto et al. | 436/43 |

FOREIGN PATENT DOCUMENTS

| | | |
|---|---|---|
| WO | WO A 94/23300 | 10/1994 |
| WO | WO A 95/16207 | 6/1995 |
| WO | WO A 95/16208 | 6/1995 |
| WO | WO A 96/38720 | 12/1996 |

* cited by examiner

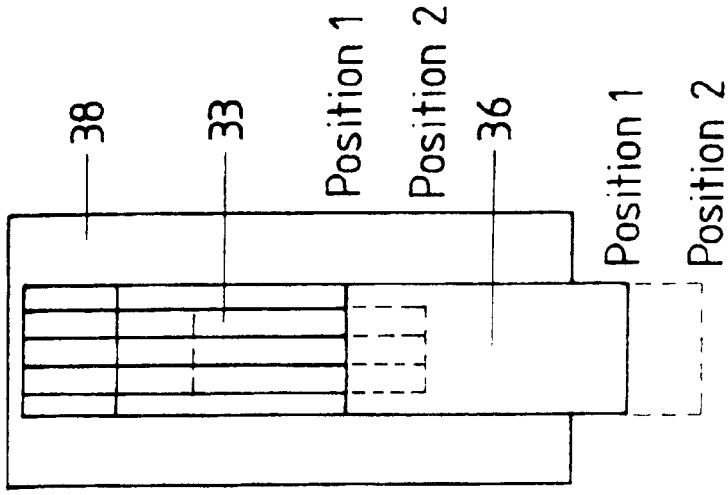
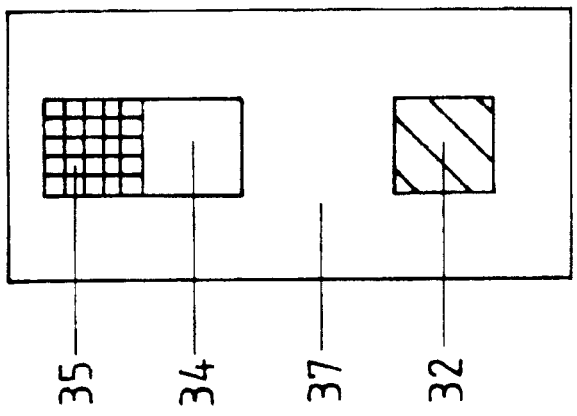
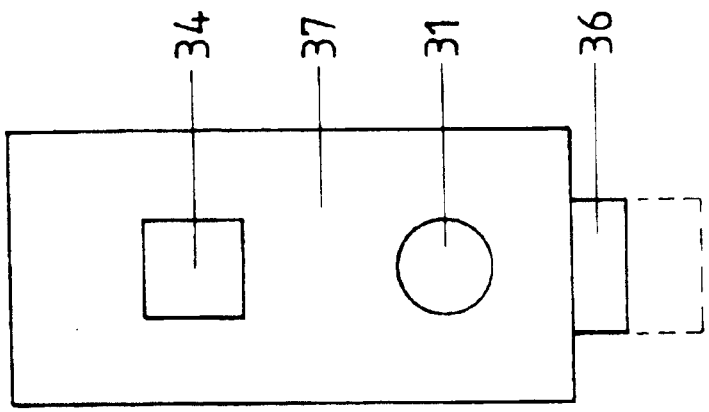

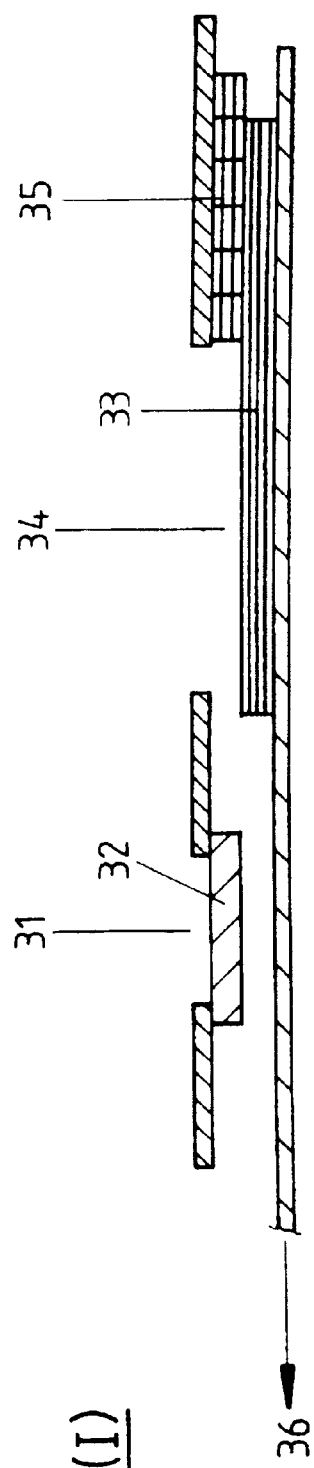
FIG 3c(I)
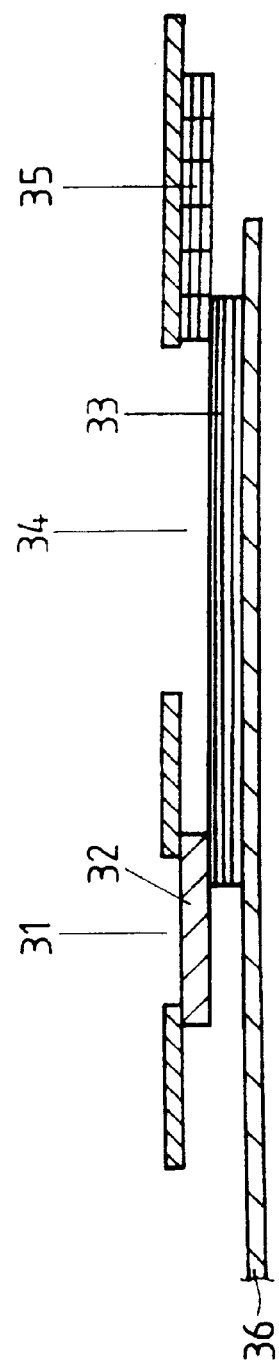
FIG 3c(II)

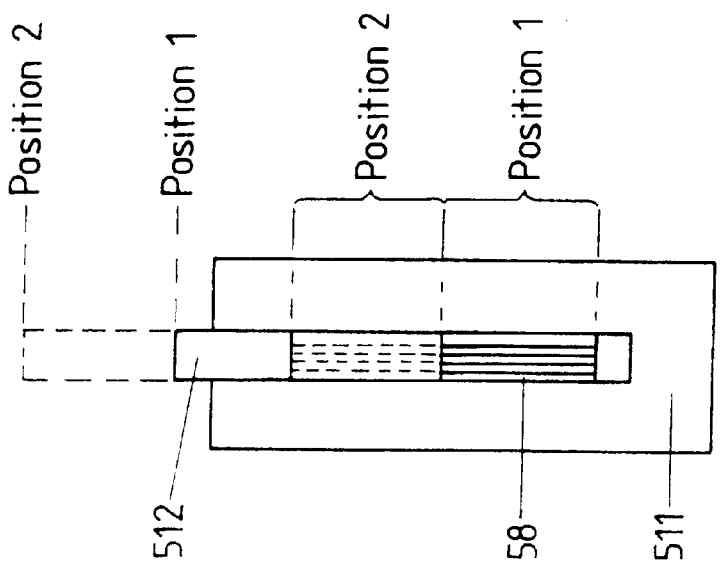
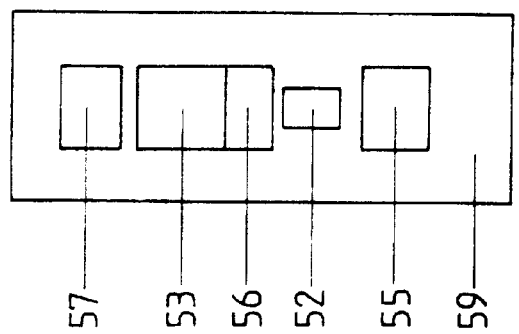
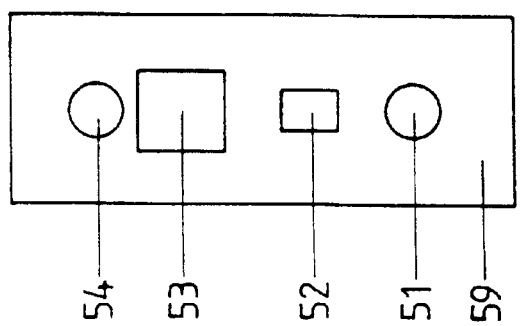

Position 1        Position 2

CHROMATOGRAPHIC ASSAY OR TEST DEVICE

FIELD OF THE INVENTION

This invention relates to a chromatographic assay or test device for detection and/or determination of an analyte in a sample, and in one particular embodiment it relates to a chromatographic assay device which incorporates an immunoassay in a procedure known as immunochromatography.

This invention has particular, but not exclusive, application in the detection of analytes in biological samples such as blood, urine, faecal and saliva samples, and the like.

BACKGROUND OF THE INVENTION

Prior International Patent Applications Nos. PCT/US92/00425(WO 92/21977) and PCT/US94/13982 (WO 95/16207) note that among the many analytical systems used for detection and/or determination of analytes, particularly analytes of biological interest, are chromatographic assay systems. Among the analytes of biological interest frequently assayed with such systems are:

1. hormones, such as human chorionic gonadotropin (hCG), frequently assayed as a marker of human pregnancy;
2. antigens, particularly antigens specific to bacterial, viral, and protozoan pathogens, such as Streptococcus, hepatitis virus, Giardia, feline leukaemia virus, tobacco mosaic virus, Salmonella, and Plasmodium;
3. antibodies, particularly antibodies induced as a result of infection with pathogens, such as antibodies to the bacterium *Helicobacter pylori*, to human immunodeficiency virus (HIV) and to feline immunodeficiency virus (FIV);
4. other proteins, such as haemoglobin, frequently assayed in determinations of faecal occult blood, an early indicator of gastrointestinal disorders such as colon cancer;
5. enzymes, such as aspartate amino transferase, lactate dehydrogenase, alkaline phosphatase, and glutamate dehydrogenase, frequently assayed as indicators of physiological function and tissue damage;
6. drugs, both therapeutic drugs, such as antibiotics, tranquillisers and anticonvulsants, and illegal drugs of abuse, such as cocaine, heroin, and marijuana;
7. vitamins; and
8. environmental contaminants, such as pathogens, herbicides, pesticides, toxic residues, and the like.

Such chromatographic systems are frequently used by physicians and medical technicians in the health field, and by agricultural and environmental professionals and technicians, for rapid point-of-care or on-site diagnosis, detection or monitoring of analytes of biological interest. They are also increasingly used by patients themselves for at-home monitoring of a variety of therapeutic conditions and disorders.

Among the most important of such chromatographic systems are the "thin layer" systems in which a solvent moves as a solvent front across a thin, flat absorbent medium. Among the most important of tests that can be performed with such thin layer systems are immunoassays, which depend on the specific interaction between an antigen or hapten and a corresponding antibody. The use of immunoassays as a means of testing for the presence and/or amount of clinically important molecules has been known for some time.

As previously noted chromatographic techniques used in conjunction with immunoassays are known as immunochromatography. In general, this technique uses a disclosing reagent or particle that has been linked to an antibody to the analyte to be assayed, forming a conjugate. This conjugate is then mixed with a specimen and, if the analyte to be assayed is present in the specimen, the disclosing reagent-linked antibodies bind to the analyte to be assayed, thereby giving an indication that the analyte to be assayed is present. The disclosing reagent or particle can be identifiable by colour, magnetic properties, radioactivity, specific reactivity with another molecule, or another physical or chemical property. The specific reactions that are employed vary with the nature of the analyte being assayed and the sample to be tested.

Although useful, currently available chromatographic techniques using test strips have a number of drawbacks. Many samples, such as faecal samples, contain particulate matter that can clog the pores of the chromatographic medium, greatly hindering the immunochromatographic process. Other samples, such as blood, contain cells and coloured components that make it difficult to read the test. Even if the sample does not create interference, it is frequently difficult with existing chromatographic test devices to apply the sample to the chromatographic medium so that the solvent front moves uniformly through the chromatographic medium to ensure that the sample reaches the area where binding is to occur in a uniform, straight-line manner.

Most immunochromatographic assay or test devices, because of their fixed and inflexible formats, are limited in their range of diagnostic applications. Most allow only unidirectional liquid flows and require that specimen or sample pre-treatments, such as antigen extraction, are carried out "off-board" or prior to addition to the assay or test device.

U.S. Pat. No. 5,415,944 (assigned to Quidel Corporation) discloses a closed test device which is adapted to allow "on-board" pre-treatment, or extraction, of a specimen on a swab. In this case, the swab is inserted into an extraction chamber, which is moulded as part of the housing of the test device. Extraction reagents are added to the swab and, after a period of time, unidirectional flow follows passively as the reagents migrate from the chamber to the wicking components of the immunochromatographic test system encased within the housing.

International Patent Application Nos. PCT/US92/04425 and PCT/US94/13982 (assigned to SmithKline Diagnostics, Inc.) mentioned above, disclose testing systems involving sample preparation means or test components placed on the opposing panels of an open two-panel test device. In this case, the test is only initiated or completed on bringing the two opposing panels together on closure of the test device.

It is an object of the present invention to provide an assay or test device utilising a chromatographic assay format, more particularly an immunochromatographic assay format, that is versatile as well as being simple and economic to manufacture. In particular, it is an object to provide an assay or test device that utilises a closed housing in association with a moveable or relocatable element that allows manipulation of liquid flows for initiation, modification and/or completion of the assay procedure.

SUMMARY OF THE INVENTION

In accordance with a first aspect of the present invention, there is provided a chromatographic assay or test device for detection and/or determination of an analyte in a test sample, which comprises (a) a base member, and (b) a chromatographic medium located in or on said base member, said base member being provided with a receptacle to receive an applicator having said sample applied thereto, said applicator being movable laterally when located in said receptacle between a first position in which said applicator located in said receptacle is out of fluid contact with said chromatographic medium, and a second position in which said applicator located in said receptacle is in fluid contact with said chromatographic medium so as to apply a sample on said applicator to said chromatographic medium.

In another aspect, the present invention provides a chromatographic assay or test device for detection and/or determination of an analyte in a test sample, which comprises (a) a base member, and (b) a second member, at least one of said base member and said second member including a chromatographic medium, and said second member being movable laterally with respect to the base member from a first position to a second position, wherein in said first position a sample to be assayed applied to one of said base and second members is out of fluid contact with said chromatographic medium, and in said second position said sample is in fluid contact with said chromatographic medium.

In yet another aspect, the present invention provides a chromatographic assay or test device for detection and/or determination of an analyte in a sample, which comprises:

(a) a base member, and (b) a second member, at least one of said base member and said second member including a chromatographic medium, and said second member being movable laterally with respect to the base member from a first position to a second position, wherein in said first position a part of the assay of a sample using said chromatographic medium is enabled, and in said second position another part of the assay of said sample using said chromatographic medium is enabled.

Preferably, in each of the above aspects, the device of the invention is an immunochromatographic assay device which includes an immunochromatographic medium.

The present invention also extends to a method for the detection and/or determination of an analyte in a sample, characterised in that a chromatographic assay or test device as broadly described above is used in the method.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

DETAILED DESCRIPTION OF THE INVENTION

The present invention particularly relates to immunochromatographic test systems, but should not be seen as confined to these systems.

Immunochromatographic test systems typically consist of an assemblage of some or all of the following components:

a test housing with ports for addition of specimen and/or reagents, or which acts as a window for reading of a test result.

a sample receiving member eg. an absorbent matrix. This component may also effect some sample pre-treatment (eg. extraction) or some physical separation such as separating blood plasma from red cells.

a conjugate pad which contains an identifiable tag or label conjugated to a specific binding partner to the analyte of interest.

a liquid conductive solid phase (eg. nitrocellulose, nylon, etc.) to, on, or in which is immoblised a second specific binding partner of the analyte.

a liquid absorbent material to act as a specimen and reagent sink.

other conductive membranes, reagent pads or supports as required for the particular application.

In the various devices of the present invention, the base member and the second member (where present) may be made of any suitable material including, for example, plastics materials such as polycarbonate, polyethylene, Mylar, vinyl, cellophane and polystyrene, and well as waterproofed or water-resistant cardboard or similar material. Preferably, the base and second members are made of laminated cardboard that is sufficiently impervious to moisture to contain the liquids involved in the performance of the assay carried out by the device. Alternatively, the base and second members can be made of a plastic that is impervious to moisture, such as the polycarbonate plastic known as Lexan, polyvinylchloride, polypropylene, polyethylene, polystyrene, and the like.

Preferably the base member of the device of the present invention comprises upper and lower panels which are joined together to form a test housing. In the first aspect as broadly described above, the receptacle to receive an applicator such as a swab, dipstick or other sample or specimen collection device is conveniently provided in a lower panel of the base member with the chromatographic medium being attached to either the upper side of the lower panel or the lower side of the upper panel of the base member.

Where the device of this invention comprises a base member and a second member which is movable with respect to the base member, the base member preferably comprises upper and lower panels which are generally square or rectangular in shape and which are joined along opposite longitudinal edges so as to form a test housing. Preferably, the second member then comprises a generally square or rectangular planar member which is received within, and is slidably movable within, the test housing between the upper and lower panels.

The chromatographic medium in the device is typically a substantially planar strip, although this is not required in all applications. Typically, the chromatographic medium comprises a solid phase which is generally rectangular in shape having first and second ends. Throughout this description, the term "first end" refers to the end in which liquid is first applied to chromatographic medium and the term "second end" applies to the opposite end of the chromatographic medium. The liquid applied at or near the first end of the solid phase of the chromatographic medium can be, but is not necessarily, a sample or a treated sample. The solid phase of the chromatographic medium is composed of an absorbent or porous material suitable as a medium for thin layer chromatography of analyte and analyte-antibody conjugates, such as nitro cellulose, nylon, rayon, cellulose, paper, silica or non-woven or porous synthetic materials. This chromatographic medium can be pretreated or modified as needed. Typically, this chromatographic medium is translucent, so that coloured zones appearing on it can be viewed from either side.

In a number of devices according to the present invention, absorbers are in operable contact with one or both ends of the chromatographic medium. Such absorbers can be made of any suitable material that will hold a liquid, particularly an aqueous liquid, sufficiently that the liquid can be drawn through the chromatographic medium and accumulated in the absorber. Typically materials for such absorbers include, but are not limited to, filter paper.

Further description of elements common to devices according to the present invention for the performance of chromatographic assays or tests are fully described in International Patent Application Nos. PCT/US92/04425 and PCT/US94/13982 mentioned above, the contents of which are incorporated herein by reference.

In a first aspect, the present invention provides a device which comprises a base member which is provided with a receptacle to receive an applicator having a test sample applied thereto. Suitably, such a receptacle is formed as an elongate well in the base member shaped to accept a swab, dipstick or similar collection device having a test sample applied thereto. The elongate well is suitably constructed that the applicator or collection device can be received within the elongate well in a first position out of liquid contact with the chromatographic medium of the test device, and at this first position the test sample on the applicator or collection device may be treated with appropriate extraction or other reagents prior to the applicator or collection device being moved within the elongate well to a second position in which it is in liquid contact with the chromatographic medium so as to apply the test sample to the chromatographic medium.

In particular embodiments, the base member in the device of the present invention may comprise separate upper and lower panels, with the chromatographic medium being attached to the upper panel and the lower panel being formed with an integral elongate well, for example by vacuum forming the lower panel from a suitable plastic material such as polyvinyl chloride. Alternatively, the lower panel may be formed of a suitable cardboard or plastic with a punched aperture defining a suitable elongate well, with a flexible fluid impervious membrane overlay being provided over the punched hole so as to define the elongate well. A preferred device in accordance with this aspect of the invention is more fully described with reference to FIGS. 1 and 2 below.

In other aspects of the present invention as broadly described above, the device comprises a base member and a second member with the second member being movable with respect to the base member from a first to a second position. Preferably, this movement is a sliding movement of the second member with respect to a test housing which comprises the base member as broadly discussed above. Preferably, also the base member provides an elongate housing and the second member is an elongate member which is slidably movable between the first and second positions within this housing. Particular embodiments of these aspects of the present invention are described in detail in FIGS. 3–8 below.

BRIEF DESCRIPTION OF THE DRAWINGS

Various features of a number of embodiments of the present invention are illustrated by way of example in the accompanying drawings which are included by way of illustration, and not limitation of this invention. In the accompanying drawings:

FIGS. 1 comprises (*a*) a plan view and (*b*) a cross sectional view of a chromatographic assay or test device in accordance with a first aspect of the present invention.

FIGS. 3 comprises (*a*) plan views and (*c*) side elevations of a chromatographic assay or test device in accordance with a second aspect of the present invention.

Referring firstly to FIG. 1, there is shown an assay or test device in which an applicator, particularly a specimen collection device such as a swab or dipstick, when fully inserted, effects a liquid conducting bridge between the applicator and a chromatographic test strip, particularly an immunochromatographic test strip, thereby initiating the development of the test.

Figure 1A:
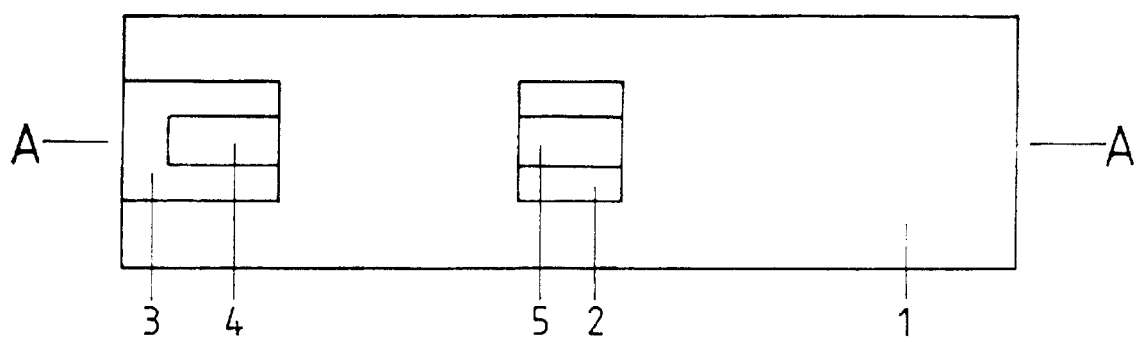
FIG. 1*a* is a plan view of a test device of this type which comprises an base member 1 consisting of upper and lower panels forming a test device housing and containing a window 2 for reading of the test result. The housing also contains an opening 3 in the upper panel thereof for insertion of a swab, dipstick or other specimen collection device. An immunochromatographic test strip 5 is located on the underside of the upper panel of the base member 1 and is covered by a protective barrier 6 leaving exposed a first end 8 of the test strip 5. An elongate well or reagent reservoir 4 is formed in the lower panel of the base member 1.
Figure 1B:
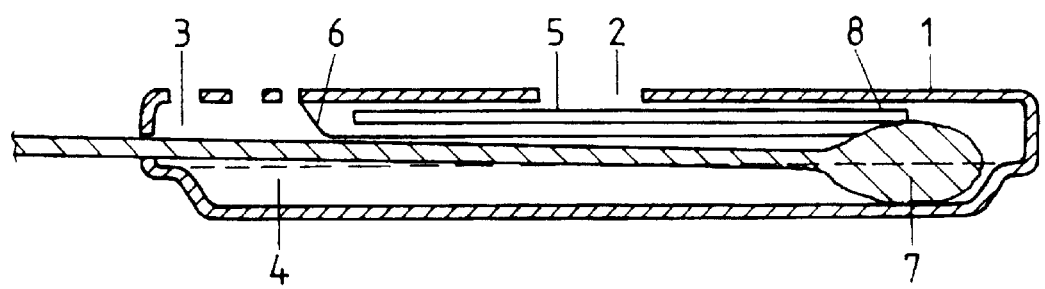
FIG. 1*b* shows a cross section along the line A—A of the device of FIG. 1*a*, with a swab 7 fully inserted into the well or reagent reservoir 4 of the device.

The closed test device shown in FIGS. 1*a* and 1*b* comprises a test device housing comprising the upper panel which houses or accommodates the immunochromatographic test strip 5 enclosed at all but its first end or origin 8 by the liquid impermeable protective barrier 6. The lower panel of the test device housing has an elongate well adapted to receive a swab, dipstick or other specimen collection device via opening 3 in the housing. The elongate well may receive reagents, via the opening 3, before, during or after insertion of the swab, dipstick or other specimen collection device. Alternatively, the elongate well may act as a reagent reservoir by having appropriate reagents prepackaged within the well by means of flexible packaging and frangible seals. In this alternative, insertion of the swab, dipstick or other specimen collection device into the elongate well would rupture the seal(s), thus exposing the specimen collection device to the reagent(s).

In many cases, it is beneficial to expose a sample on a specimen collection device to the appropriate reagent(s) for some period of time prior to initiation of the test development, for example, to effect solubilisation or extraction of diagnostically significant antigens. he test device shown in FIGS. 1*a* and *b* is designed so that partial insertion of the specimen collection device 7 into the elongate well 4 locates the device 7 at a first position enabling reagent addition to the test sample without the initiation of the test development. After allowing time for extractions/ solubilisation of antigens in the sample, full insertion of the device 7 to a second position as shown in FIG. 1b then establishes liquid contact between the device 7 and the first end or origin 8 of the immunochromatographic test strip 5. Test development is thus initiated and continues until reagent or specimen depletion, or until liquid contact is broken by partial (or full) withdrawal of the device 7.

Figure 2A:
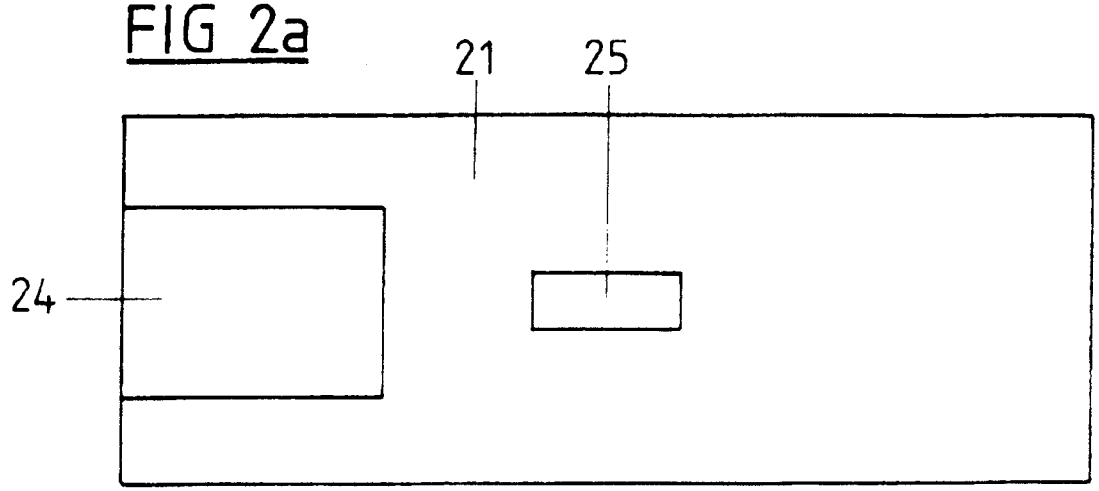
FIG. 2 is an exploded view of an alternative embodiment of the base member of the device of FIG. 1.
Figure 2B:
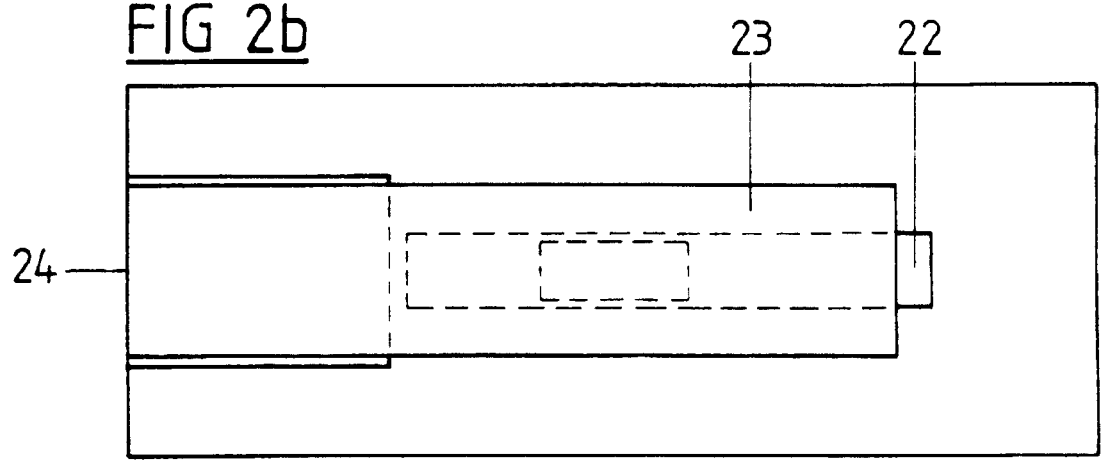
Figure 2C:
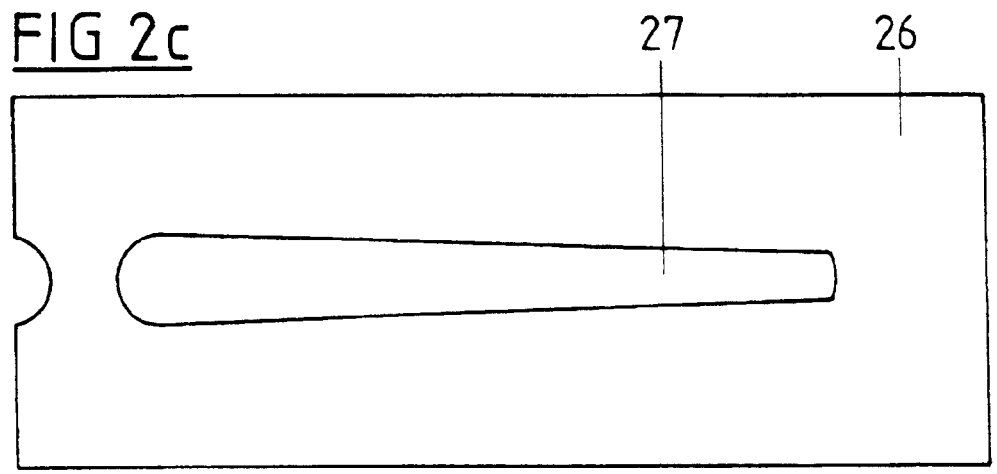

FIG. 2 shows an alternative design of the base member of the device of FIG. 1. In the alternative device, the housing comprises upper and lower panels 21 and 26, respectively. As shown in FIG. 2(a), the upper panel 21 has a hinged "door" 24 for insertion of a swab, dipstick or other specimen collection device and for addition of reagent(s), together with a window 25 for reading of the test results. FIG. 2(b) shows the underside of the upper panel 21 which has affixed thereto an immunochromatographic test strip with all but its sample receiving first end or origin 22 protected by a moisture impermeable protective barrier 23. Upper panel 21 is preferably made of laminated cardboard or plastic, and is designed to be mass produced by dye-cutting and printing, with component lay down by a high-speed, fully automated assembly process. FIG. 2(c) shows the lower panel 26, with integral elongate well 27. This lower panel is preferably vacuum formed from a suitable plastics material, such as polyvinyl chloride. Alternatively, a laminated cardboard or plastic panel may be used, with a punched hole defining a suitable elongate well, and a flexible moisture impermeable membrane overlaying the punched hole to form the elongate well. As previously described, the elongate well may also be adapted to housing pre-packaged reagent(s) so that insertion of a specimen collection device liberates the reagents to the sample on the specimen collection device.

Assembly of the device shown in FIG. 2 would consist of binding the upper panel to the lower panel. The lower panel would preferably be formed in situ and bound to the upper panel using a high speed fully automated form/fill/seal machine, as used for blister packaging many inexpensive, mass produced consumer products.

In the embodiments of the invention shown in FIGS. 3–8, the components of a closed test device are moveable with respect to other another so that they may be repositioned during the course of a test (including for initiation and at completion) in order to manipulate or control application of a test sample and various liquid flows, and hence the development of the test. Accordingly, the device of the present invention, by allowing flow control through the repositioning of components within a closed test device, allows a wide range of test procedures to be simply and efficiently completed.

FIG. 3 illustrates a closed assay or test device with utilises a period of static pre-incubation of the sample with conjugate prior to commencement of reagent flow and capture in a chromatographic medium.

FIG. 3(a) shows a closed test device comprising a housing or base member including upper panel 37 which includes sample addition port 31 together with window 34 for reading the results of the assay or test. The housing or base member also comprises lower panel 38 as shown in FIG. 3(b)(ii). A second member in the form of movable element 36 is formed as a sliding panel movable from a first position to a second position with respect to the base member FIG. 3(b)(i) shows the underside of the upper panel 37 and shows conjugate pad 32 affixed to the underside of the upper panel 37 below the sample addition port 31, together with an absorbent pad 35. Immunochromatographic test strip 33 is affixed to the second member 36 which is movable from a first position (solid lines) to second position (broken lines).

FIG. 3(c)(i) is a side elevation of the device of FIG. 3a with the components in the first position. Sample is added to the conjugate pad 32 through the port 31 and reconstitutes the conjugate. No flow is possible so a pre-incubation step between the conjugate and analyte in the sample can take place. FIG. 3(c)(ii) shows the component of the device in the second position in which movable second member 36 has been moved so that the origin of the immunochromatographic test strip 33 is in liquid-contact with the sample/conjugate mixture in conjugate pad 32. Flow of reagent and test development may now take place, via the immunochromatographic test strip 33 (which will incorporate a capture band) to the absorbent 35.

As described above, preferred designs in this aspect of the present invention use a three-panelled base member or housing in which the upper and lower panel are attached in such a way as to control and guide a movable middle panel or second member. The test components may be affixed to any of the panels in any manner required to meet the requirements for completing the particular test.

FIG. 4 illustrates an alternative embodiment of the test device shown in FIG. 3 based on the test requirements and component placements previously described in FIG. 3 enabling a period of pre-incubation of a sample with a conjugate before commencement of flow/capture.

Figure 4A:
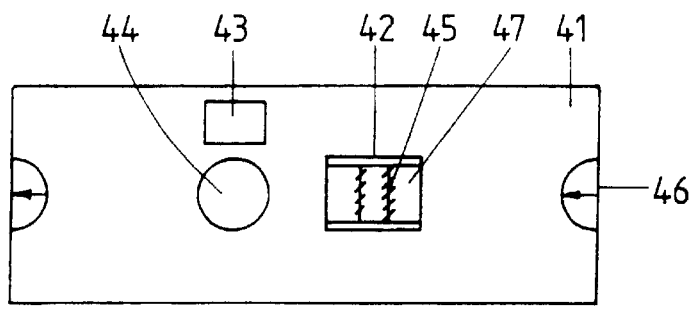
FIG. 4 comprises a series of plan views of another embodiment of a device in accordance with the second aspect of the invention.

FIG. 4(a) shows the test device 41 in the first or closed position. The base member of the device comprises an upper panel 413 having a window 42 through which result lines 45 on the solid phase 47 may be observed. The specimen port 44 is closed in the first position, and an instruction window 43 may be blank or have a printed instruction about proceeding to the second position of the test.

Figure 4B:
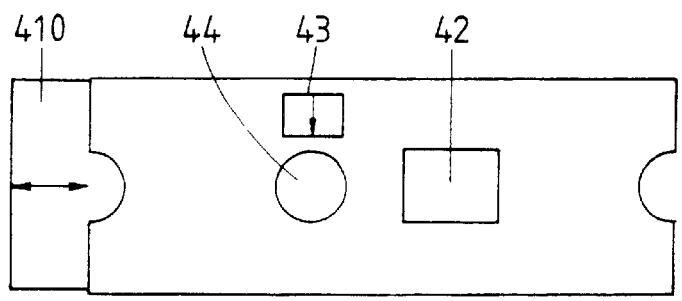

Pressure applied at point 46 causes displacement of the movable panel 410 forming the second member to the second position as shown in FIG. 4(b). In this position, the specimen port 44 is open and the instruction window 43 may have an instruction about addition of the test sample to the port 44. The result window 42 is closed by the sliding panel 410 while the device is in the second position.

Figure 4C:
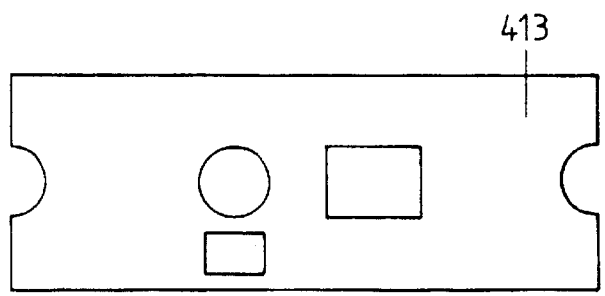
Figure 4D:
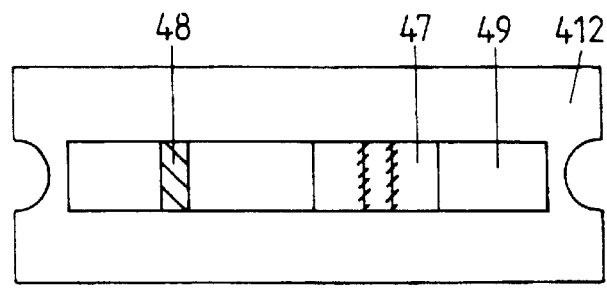

FIG. 4(c) shows the underside of the upper panel 413 which together with lower panel 412 makes up the base member of the device. FIG. 4(d) shows the upper side of the lower panel 412 with an immunochromatographic test strip 49 affixed thereto. Test strip 49 consists of the solid phase 47 as well as a stop 48, which together with a similar stop 415 shown in FIG. 4(e), acts to prescribe the range of displacement of the movable panel 410.

Figure 4E:
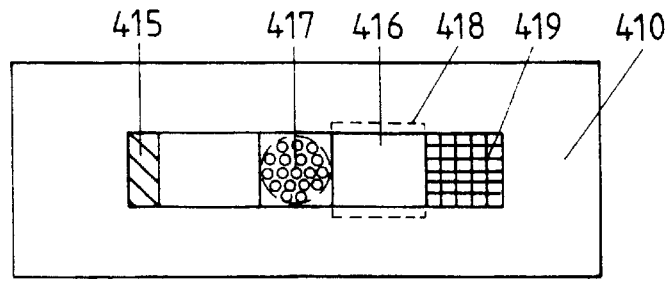

FIG. 4(e) shows the underside of the movable middle panel 410. A clear plastic support strip 416 pre-laminated with a stop 41 5, conjugate pad 417 and absorbent 419 is affixed to the panel. The panel has a window 418 (as shown in dotted outline) which coincides with the window opening 42 of the upper panel when the test is in the first position. Conjugate pad 417 is accessed by a hole or perforation (dotted) in panel 410 and a corresponding hole or perforation in support strip 416. The upper side of the movable panel 410 may be printed with instructions placed to appear in the instruction window 43 in the first and second positions. The upper and lower panels 413 and 412 may be joined by tape at the longitudinal edges thereof so that the middle panel 410 remains free to slide within the base member of the device. This format is designed to be suited to inexpensive, high speed, fully automated assembly procedures, for example, the panels may be die cut, printed and the relevant components affixed in one continuous operation. At this stage, the panels may be stacked and stored in a magazine until required for completion of assembly. The three panels may then be fed from the magazines to a nest on a conveyor belt, the edges taped, and the assembled device packaged into a hermetically sealed bag in one further operation.

The test procedure for a device as shown in FIG. 4, is firstly to move the movable middle panel 410 to the second position and add sample to the reagent port 44. In this position, the conjugate pad 417, accessed through the specimen port 44 and corresponding holes or perforations in panel 410 and support strip 416, is disconnected from the solid phase 47 so no flow/capture occurs. After a period for pre-incubation of the sample with the conjugate in pad 417, the movable panel 410 is returned to the first position. This establishes contact between the conjugate pad 417 and the solid phase 47 of the immunochromatographic test strip 49, allowing development of the assay or test. The result may be read through the result window 42.

Figure 5C:
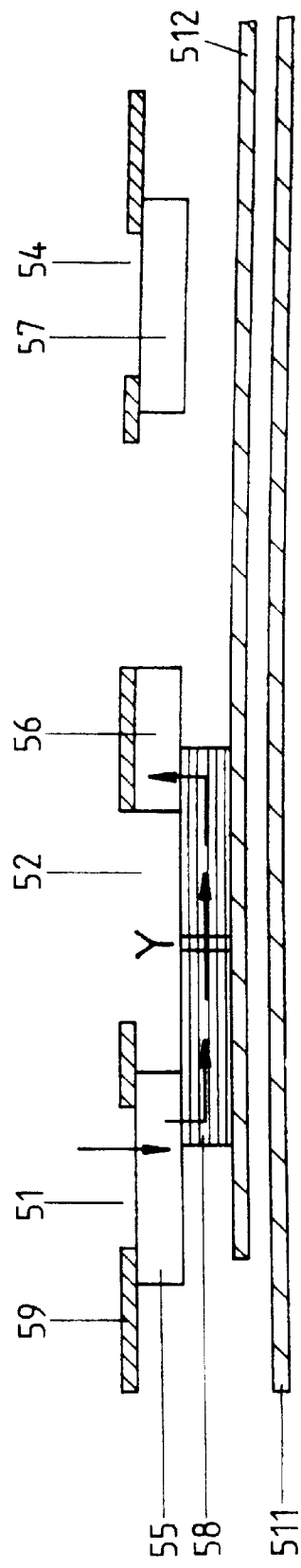
FIGS. 5 comprises (*a*) plan views and (*c*), (*d*) side elevations of a chromatographic assay or test device in accordance with a third aspect of the present invention.
Figure 5D:
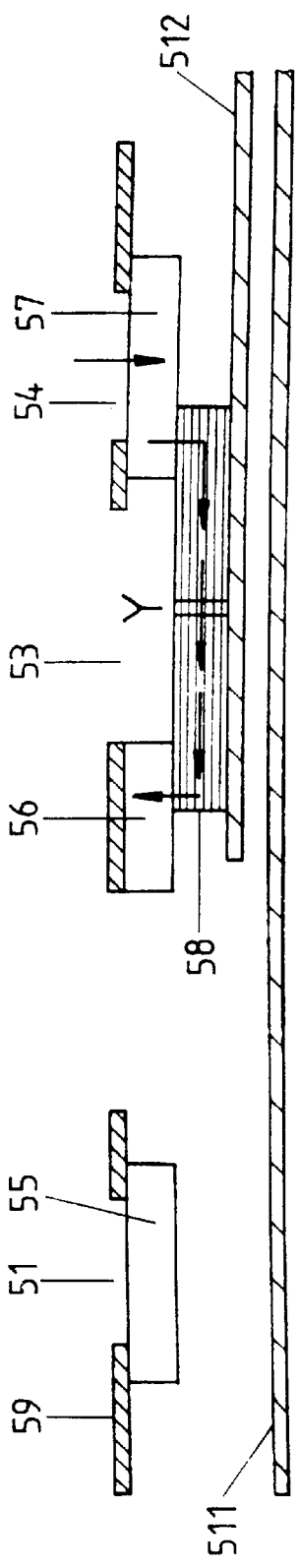

FIG. 5 illustrates another embodiment of the device of the present invention which includes the use of forward flow of sample along the solid phase for capture of the analyte in the sample, followed by reverse flow along the solid phase for labelling. The ability to conduct forward and reverse flows along the solid phase is an advantage in several assay types. For example:

Heavily pigmented specimens (eg. lysed blood), obscure the visual assessment of a developing colour at the detection (capture) line of the solid phase. The ability to reverse the flow with, for example, a clean wash solution enables the result to be clearly seen.

In some test applications, the conjugate bound to the analyte may sterically hinder the efficient capture of the complex at the capture line.

For serological assays, the specific antibody of interest may be captured on forward flow and labelled on reverse flow. Interference from the vast excess of non-specific antibody prevents the use of other assay configurations for serological assays.

FIG. 5a shows an embodiment of a device utilising both forward and reverse flows and shows the upper face of upper panel 59 of the base member forming a test housing. The upper panel includes a specimen port 51, a window 52 for confirming flow of reagent, a window 53 for reading the results of the test or assay together with a reagent port 54.

FIG. 5(b)(i) shows the lower face of the upper panel 59 of the test housing which has affixed thereto a sample or specimen pad 55, an absorbent pad 56 and a reagent pad 57. FIG. 5(b)(ii) shows movement of a movable second member 512 having the immunochromatographic solid phase 58 affixed thereto, from a first position to a second position with respect to the lower panel 511 of the base member of the test housing.

FIGS. 5(c) and (d) show the positioning of the movable member 512 with respect to the base member or test housing and reagent flows in the first and second positions, respectively. With the components in the first position, forward flow of reagents and capture of the analyte in the sample is enabled. The sample is added via the specimen port 51 to the specimen pad 55. Flow of specimen occurs along the solid phase 58 in the direction shown by arrows into the absorbent pad 56 (the flow may be observed via a window 52 and may continue until reagent/specimen depletion or until the components are moved to the second position). In the second position, reverse flow of reagents provides for labelling. Liquid is added through the reagent port 54 to reconstitute conjugate in the conjugate pad 57. Conjugate flows along the solid phase 58 into the absorbent 56 and the result may be observed through the window 53.

As noted above, this assay format is particularly suitable for serological assays. For example, for the detection of antibodies to HIV in human blood, the procedure using this device would be as follows:

(i) With the components in the first position human blood is added via the port 51 to a blood separation membrane 55. Plasma flows via the solid phase 58 and antibodies against HIV bind to a band of HIV-specific antigen immobilised in the solid phase at Y.

(ii) After a specified flow time or distance, the components are moved to the second position. Liquid (eg. buffer) added through port 57 causes conjugate (anti-human IgG) conjugated to a visible label to flow down the solid phase 58 and bind to any human antibodies captured at Y. An accumulation in colour at Y is observed through the window 53.

Figure 6:
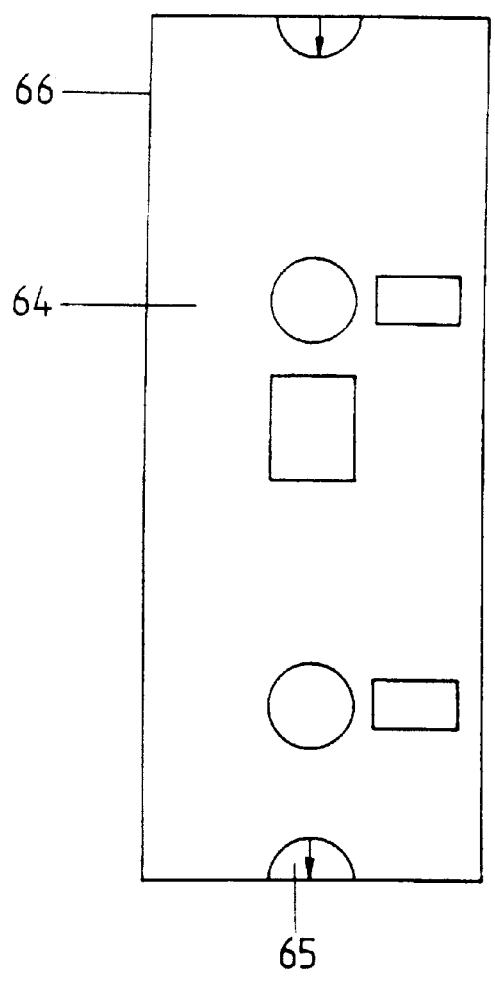
FIG. 6 shows plan views of another embodiment of a device in accordance with the third aspect of the invention.
Figure 6:
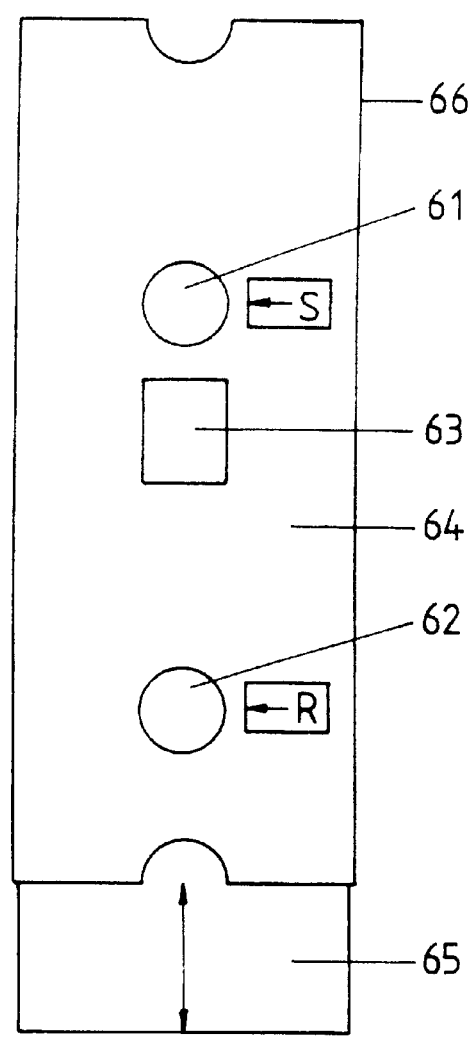

FIG. 6 illustrates a variant of the format of FIG. 5 and the component placements and reagent flow paths are as described with regard to FIG. 5. Device 64 is issued with the second member 65 in its first position with respect to the base member or test housing 66. To conduct a test, the member 65 is moved to the second position (defined by internal stops), and specimen is added to the specimen port 61 in accordance with instructions provided in the instruction window (S). Reagent is added to the reagent port 62 in accordance with instructions given in instruction window (R) in order to reconstitute conjugate contained in the conjugate pad under the port 62. Member 65 is then returned to the first position with respect to the test housing 66 and by this action the ports and instruction windows close, the specimen pad is disconnected from the solid phase, the conjugate pad makes contact with the solid phase and reverse flow labelling and test development flow as described with respect to FIG. 5. The test result is then read in the window 63.

The device shown in FIG. 7 is particularly adapted for use in antigen detection procedures, for example in detection of antigens specific to bacterial, viral and protozoan pathogens in blood samples. The test device of FIG. 7 comprises upper and lower panels, 710 and 711, shown in FIGS. 7a and 7b respectively, together with a sliding panel 712, shown in FIGS. 7c and 7d which slides within a test housing formed by the upper and lower panels which are joined along the longitudinal edges thereof to form this housing. Upper panel 710 includes a reagent port 78 and window 79 for observing the results of the test development. Test strip 71 is located on the lower panel 711 and comprises an absorbent pad 72 and a conjugate pad 73 with the solid phase of the immunochromatographic medium 74 located between these pads. Test strip 71 is overlaid with a clear protective membrane 75 which protects the absorbent pad 72 from wetting by plasma from a blood sample applied to the assay device when the sliding panel 712 is returned to the first position for development of the test result. Protective membrane 75 is provided with a hole or perforation therein coinciding with the conjugate pad 73.

Figure 7D:
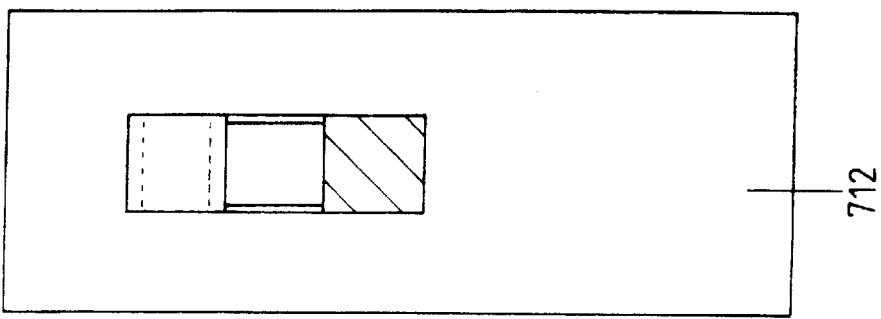
FIG. 7 depicts a further embodiment of a chromatographic assay or test device in accordance with this invention which is particularly suited for antigen assay procedures which use blood as the test specimen.
Figure 7C:
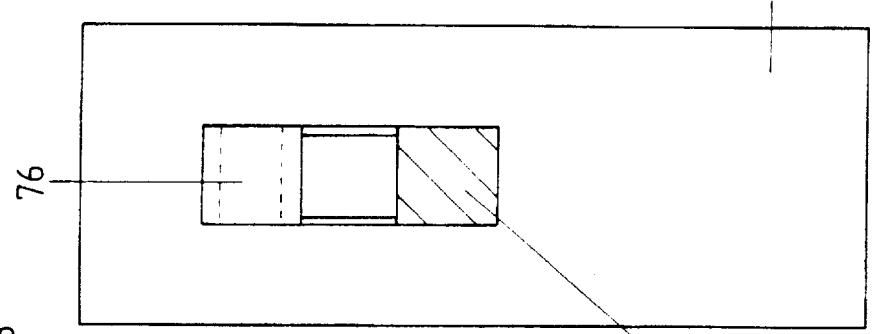
Figure 7B:
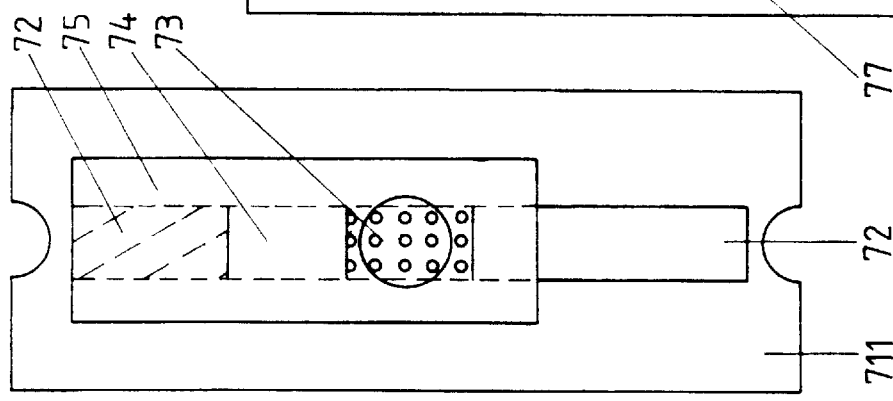
Figure 7A:
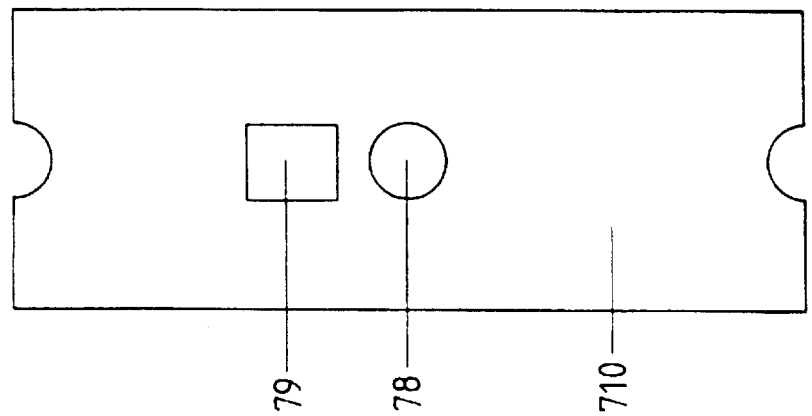
Figures 7E, 7F:
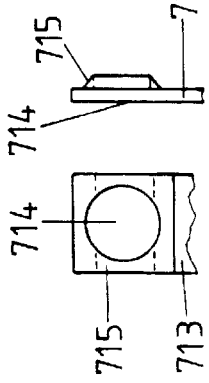

As shown in FIGS. 7c and 7d, sliding panel 712 is provided with a reagent pad 77 together with a blood separation module 76, shown in greater detail in FIGS. 7e and 7f. Referring to FIGS. 7e and 7f, the blood separation module comprises a backing strip having a port 714 formed therein. Port 714 is covered by an absorbent matrix and a blood separation membrane 715, preferably a multi layer separation membrane such as a MPS membrane (available from Spectral Diagnostics Inc., Toronto, Ontario, Canada).

In the use of the device shown in FIG. 7, sliding panel 712 is moved to the second position as shown in FIG. 7c, and a blood sample is added to the device through the open port 78 in the upper panel 710. Plasma is separated from the blood sample by separation module 76, and as the separation module 76 is in contact with the conjugate pad 73 in this position, plasma permeates the conjugate pad 73. After a suitable time, for example 1 minute, the sliding panel 712 is moved to the first position where the separation module 76 moves over the absorbent pad 72 (but the absorbent pad 72 is protected from wetting by plasma from the separation module 76 by the protective membrane 75). In this position, the reagent pad 77 contacts the conjugate pad 73. An appropriate amount of developer reagent is added to the reagent pad 77 through the open port 78 so that the added reagent displaces the conjugate/plasma mixture along the solid phase 74 to the absorbent pad 72. After an appropriate time, the test result is observed through the window 79.

Figure 8:
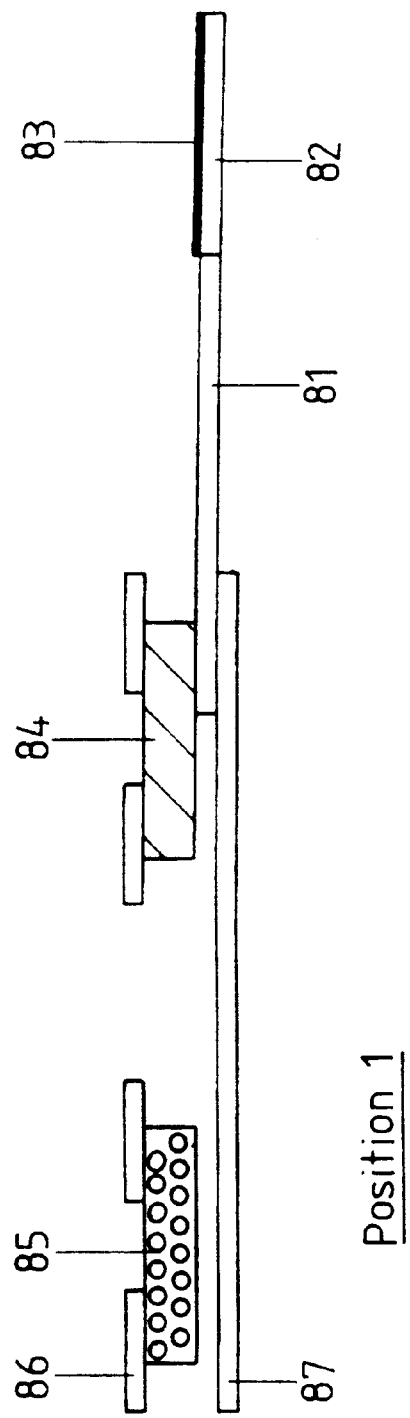
FIG. 8 shows diagrammatically yet another embodiment of an assay or test device in accordance with this invention.
Figure 8:
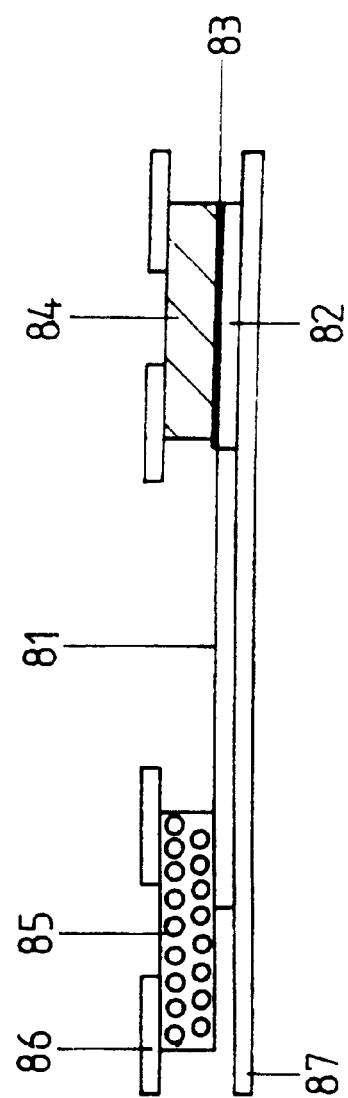

FIG. 8 shows diagrammatically a further embodiment of the assay or test device of the present invention which operates on similar principles to the device shown in FIG. 5, however whereas the device of FIG. 5 operates using both forward and reverse flow in sequence, with capture on forward flow followed by labelling on reverse flow, the device of FIG. 8 is designed to enable these sequential assays to be conducted using forward flow only, that is with the sample and the conjugate being applied in sequence to the same end or origin of the chromatographic medium.

The device shown in FIG. 8 comprises a base member of test housing made up of an upper panel 86 and lower panel 87. Upper panel 86 is provided with appropriate ports and windows for addition of reagents and samples and for observing test results. On the underside of upper panel 85 are located a sample application pad 84, which may comprise a blood separation module as described with reference to FIG. 7 above, and a conjugate pad 85. The second member of the device of FIG. 8, which is movable with respect to the test housing comprising panels 86 and 87 between first and second positions as shown, comprises a chromatographic medium 81 in liquid contact at one end with an absorbent pad 82 which is overlaid with a liquid-impermeable barrier membrane 83.

In use of the device shown in FIG. 8, the device is initially set up in the first position as shown where the sample application pad 84 is in contact with the first end or origin of the chromatographic medium 81. The sample is applied to the application pad 84 and flows up the chromatographic medium into the absorbent pad 82. After an appropriate period of time, the second member is moved to the second position as shown where the conjugate pad 85 is brought into contact with the first end of origin of the chromatographic medium 81. Sample application pad 84 is positioned above the absorbent pad 82 and since the absorbent pad is overlaid with the barrier membrane 83, sample pad 84 is out of liquid contact with the chromatographic medium in this position. Addition of reagent to conjugate pad 85 applies conjugate to the first end or origin of the chromatographic medium 81 and enables flow of conjugate along the chromatographic medium for development of the assay.

It will be appreciated by a person skilled in this art that whilst a number of particular embodiments of the present invention have been described in detail above and are shown in the accompanying figures, many variations and alterations may be made to these embodiments without departing from the spirit and scope of the present invention as broadly described above. Accordingly, the present invention extends to all embodiments of the invention which fall within the broad scope and spirit of the invention as described herein.

I claim:

1. A chromatographic assay or test device for detection and/or determination of an analyte in a test sample, which comprises:
   (a) an elongate base member comprising upper and lower panels which are joined together to form a test housing, and
   (b) a chromatographic medium located in or on said base member, said base member being provided with a receptacle formed in the lower panel of the test housing to receive an applicator having said sample applied thereto, said receptacle having an elongate well forming a reagent reservoir, said applicator being movable longitudinally with respect to the base member when located in said receptacle between a first position in which said applicator located in said receptacle is out of fluid contact with said chromatographic medium, and a second position in which said applicator located in aid receptacle is in fluid contact with said chromatographic medium so as to apply said sample on said applicator to said chromatographic medium.

2. A chromatographic assay or test device for detection and/or determination of an analyte in a test sample, which comprises:
   (a) an elongate base member comprising upper and lower panels which are joined together to form a test housing, and
   (b) a other planar member, at least one of said base member and said planar member including a chromatographic medium, and said planar member being received within said test housing and slidably movable longitudinally with respect to the base member from a first position to a second position, wherein in said first position said sample to be assayed, applied to one of said base member and said other member, is out of fluid contact with said chromatographic medium, and in said second position said sample is in fluid contact with said chromatographic medium.

3. A chromatographic assay or test device for detection and/or determination of an analyte in a sample, which comprises:
   (a) an elongate base member comprising upper and lower panels which are joined together to form a test housing, and
   (b) a planar member, at least one of said base member and said planar member including a chromatographic medium, and said planar member being received within said test housing and slidably movable longitudinally with respect to the base member from a first position to a second position, wherein in said first position only a first part of the assay in which a sample is applied to said chromatographic medium is enabled, and in said second position a further part of the assay is enabled.

4. The assay or test device according to claim 1, claim 2 or claim 3, wherein said chromatographic medium is an immunochromatographic medium.

5. The assay or test device according to claim 1, wherein the base member comprises a material selected from the group consisting of plastics materials, water-proofed cardboard and water-resistant cardboard.

6. The assay or test device according to claim 1, claim 2 or claim 3, wherein said chromatographic medium comprises a substantially planar strip.

7. The assay or test device according to claim 6, wherein said chromatographic medium comprises an absorbent or porous material selected from the group consisting of nitrocellulose, nylon, rayon, cellulose, paper, silica and non-woven and porous synthetic materials.

8. The assay or test device according to claim 1, wherein said chromatographic medium is attached either to the upper side of the lower panel of the base member, or to the lower side of the upper panel of the base member.

9. A method for the detection and/or determination of an analyte in a sample, comprising the steps of:
   (a) providing a chromatographic assay or test device according to claim 1; and
   (b) moving the applicator of claim 1 from the first position to said second position for completing the detection and/or determination of an analyte in the sample.

10. The assay or test device according to claim 2 or claim 3, wherein said upper and lower panels are generally square or rectangular in shape and which are joined along opposite longitudinal edges.

11. The assay or test device according to claim 10, wherein said planar member comprises a generally square or rectangular planar member.

12. The assay or test device according to claim 11, wherein said chromatographic medium comprises an immunochromatographic test strip which is located on said planar member, and in said first position said test strip is out of fluid contact with a sample or conjugate pad located on the underside of the upper panel of the test housing, while in said second position said test strip is in fluid contact with said sample or conjugate pad.

13. The assay or test device according to claim 11, wherein said chromatographic medium comprises an immunochromatographic test strip which is located on the upper side of the lower panel of the test housing, and in said first position said test strip is in fluid contact with a sample or conjugate pad located on said other member, while in said second position said test strip is out of fluid contact with said sample or conjugate pad.

14. The assay or test device according to claim 11, wherein said chromatographic medium comprises an immunochromatographic test strip which is located on said planar member, and said planar member is movable from said first position in which forward flow of test reagents on said test strip is enabled to said second position in which reverse flow of test reagents is enabled.

15. The assay or test device according to claim 11, wherein said chromatographic medium comprises an immunochromatographic test strip which is located on said planar member, and said planar member is movable from said first position in which capture of an analyte in a test sample on said test strip is enabled to said second position in which labeling of captured analyte is enabled.

16. The assay or test device according to claim 2 or claim 3, wherein the base member and the planar member each comprises a material selected from the group consisting of plastics materials, water-proofed cardboard and water-resistant cardboard.

17. A method for the detection and/or determination of an analyte in a sample, comprising the steps of:
   (a) providing a chromatographic assay or test device according to claim 2; and
   (b) moving the planar member of claim 2 from the first position to said second position for completing the detection and/or determination of an analyte in the sample.

18. A method for the detection and/or determination of an analyte in a sample, comprising the steps of:
   (a) providing a chromatographic assay or test device according to claim 3; and
   (b) moving the planar member of claim 3 from the fist position to said second position for completing the detection and/or determination of an analyte in the sample.

19. A chromatographic assay or test device for detection and/or determination of an analyte in a test sample, which comprises:
   (a) an elongate base member,
   (b) a chromatographic medium located in or on said base member, said base member being provided with a receptacle to receive an applicator having said sample applied thereto, said applicator being movable longitudinally with respect to the base member when located in said receptacle between a first position in which said applicator located in said receptacle is out of fluid contact with said chromatographic medium, and a second position in which said applicator located in said receptacle is in fluid contact with said chromatographic medium so as to apply said sample on said applicator to said chromatographic medium, and
   (c) an opening formed in said elongate base member for receiving a reagent to be placed in fluid contact with said applicator when said applicator is in said receptacle.

20. The chromatographic assay or test device of claim 19, further comprising,
   a protective barrier mounted inside said elongate base member,
   wherein said chromatographic medium is shielded from said receptacle along substantially an entire length of said chromatographic medium by said protective barrier.

21. The chromatographic assay or test device of claim 19 or 20, wherein an elongate well is formed within said receptacle for holding a reagent for application to said applicator.

22. A method for the detection and/or determination of an analyte in a sample, comprising the steps of:
   (a) providing a chromatographic assay or test device according to claim 22; and
   (b) moving the planar member of claim 20 from the first position to said second position for completing the detection and/or determination of an analyte in the sample.

23. A method for the detection and/or determination of an analyte in a sample, comprising the steps of:
   (a) providing a chromatographic assay or test device according to claim 20; and
   (b) moving the applicator of claim 19 from the first position to said second position for completing the detection and/or determination of an analyte in the sample.

24. A chromatographic assay or test device for detection and/or determination of an analyte in a test sample, which comprises:
   (a) an elongate base member, and
   (b) a planar member, at least one of said base member and said planar member including a chromatographic medium, and said planar member being movable longitudinally with respect to the base member from a first position to a second position, wherein in said first position said sample to be assayed, applied to one of said base and said other member, is out of fluid contact with said chromatographic medium, and in said second position said sample is in fluid contact with said chromatographic medium and said chromatographic medium is in contact with an absorbent pad, wherein said sample flows through the chromatographic medium to the absorbent pad.

25. A method for the detection and/or determination of an analyte in a sample, comprising the steps of:

(a) providing a chromatographic assay or test device according to claim 21; and
(b) moving the planar member of claim 24 from the first position to said second position for completing the detection and/or determination of an analyte in the sample.

* * * * *